United States Patent [19]

Modak et al.

[11] Patent Number: 5,133,090
[45] Date of Patent: Jul. 28, 1992

[54] ANTIVIRAL GLOVE

[75] Inventors: Shanta M. Modak, Riveredge, N.J.; Lester Sampath, Nyack, N.Y.

[73] Assignee: The Trustees of Columbia University in the City of New York, Morningside Heights, N.Y.

[21] Appl. No.: 555,093

[22] Filed: Jul. 18, 1990

Related U.S. Application Data

[63] Continuation-in-part of Ser. No. 258,189, Oct. 14, 1988, Pat. No. 5,019,096, which is a continuation-in-part of Ser. No. 154,920, Feb. 11, 1988, abandoned.

[51] Int. Cl.$^5$ ............................................. A41D 13/10
[52] U.S. Cl. ........................................ 2/168; 2/167; 604/292
[58] Field of Search ............... 2/161 R, 169, 167, 168, 2/159, 163, 243 A, 21; 128/918, 917; 604/292; 523/122

[56] References Cited

U.S. PATENT DOCUMENTS

| | | | |
|---|---|---|---|
| 4,070,173 | 1/1978 | Stockum | 2/168 |
| 4,143,109 | 3/1979 | Stockum | 264/112 |
| 4,499,154 | 2/1985 | James et al. | 2/167 X |
| 4,597,108 | 7/1986 | Momose | 2/168 |
| 4,675,347 | 6/1987 | Mochizuki et al. | 523/122 |
| 4,771,482 | 9/1988 | Shlenker | 2/161 R |
| 4,853,978 | 8/1989 | Stockum | 2/167 |
| 4,925,668 | 5/1990 | Khan | 424/422 |
| 5,019,096 | 5/1991 | Fox, Jr. et al. | 2/167 X |
| 5,031,245 | 7/1991 | Milner | 2/168 |

FOREIGN PATENT DOCUMENTS

WO90/01956 3/1990 PCT Int'l Appl. .
2218617 11/1989 United Kingdom .

OTHER PUBLICATIONS

Harbison et al., Inactivation of Human Immunodeficiency Virus . . . Journal of Acquired Immune Deficiency . . . (1989), vol. 2, No. 1, pp. 16–20.
Yamamoto et al., Antiviral Action of Benzalkonium Chloride . . . J. Antibact. Anifung. Agents (1988), vol. 16, No. 11, pp. 505–508.
Chemical Abstracts (1975) vol. 83, p. 38 71620b.
Chemical Abstracts (1984) vol. 101, p. 8 221999p.
Chemical Abstracts (1985) vol. 102, p. 304 128281j.
Journal of Controlled Release, (1987), 6. pp. 343–352, Elsevier Science Publishers B.V. Amsterdam.

Primary Examiner—Werner H. Schroeder
Assistant Examiner—Sara M. Current
Attorney, Agent, or Firm—Brumbaugh, Graves, Donohue & Raymond

[57] ABSTRACT

An antiviral surgical or examination glove is obtained by blocking adsorption sites for the antiinfective agent which may exist in the lubricating agent, e.g., cross-linked corn starch, or in the material of the glove itself. The glove of the invention comprises an elastomeric hand-shaped body having interior and exterior surfaces and an inner coating disposed on the interior surface of the elastomeric body. The inner coating comprises (a) an antiinfective agent selected from the group consisting of chlorhexidine and pharmaceutically acceptable salts of chlorhexidine and (b) a lubricating agent which does not significantly adsorb the antiinfective agent. The inner coating is effective to deliver an antivirally effective amount of the antiinfective agent within ten minutes of exposure to a liquid.

13 Claims, No Drawings

ANTIVIRAL GLOVE

This application is a continuation-in-part of U.S. patent application Ser. No. 258,189, filed Oct. 14, 1988, now U.S. Pat. No. 5,019,096 which is a continuation-in-part of U.S. patent application Ser. No. 154,920 filed Feb. 11, 1988, now abandoned.

BACKGROUND OF THE INVENTION

This application relates to antiinfective surgical or examination gloves having a quick release interior coating containing a biguanide antiinfective agent. The gloves of the invention provide rapid protection against infectious agents, including viruses, and are stable over prolonged storage periods.

Surgical and examination gloves perform a barrier function providing separation between a patient and a health care worker. In fulfilling this function, the gloves act to block the introduction of infectious agents, particularly bacteria and fungi, from the hands of the health care worker into a surgical incision or wound of the patient. In this regard, it has been recognized that bacteria present in pores of a health care worker's hands frequently survive antibacterial scrubbing to be released with perspiration into the interior of the glove. These bacteria pose a significant risk for infection if a tear or hole in the glove allows their release. Thus, antimicrobial gloves have been proposed with the intention of killing these released bacteria within the glove. U.S. Pat. No. 4,853,978 to Stockum.

The barrier function of the gloves also serves to protect the health care worker from pathogenic agents, particularly those present in the blood or other body fluids of the patient. Of particular significance in this regard are viruses, such as HIV, the virus causing Acquired Immunodeficiency Syndrome (AIDS), and Hepatitis B virus (HBV) which may even penetrate through a glove that is not actually perforated but merely stretched. Agents which are effective against these pathogenic agents, however, are less common than those that will provide an effect against simple skin bacteria or fungi and must frequently be present at much higher levels to be efficacious. This can cause difficulties for the wearer whose skin is in contact with high levels of antiinfective agent, sometimes for hours at a time. It would therefore be highly advantageous to provide gloves in which an effective virucidal agent were maintained in a "ready" state, available for quick or even instant release as needed to counter the effects of possible viral contamination.

The Stockum patent cited above provides a partial but incomplete solution to this problem. Stockum discloses gloves having an interior coating of polyurethane, starch and chlorhexidine. Chlorhexidine has the ability to kill the AIDS virus and HBV as shown in prior commonly assigned U.S. patent application Ser. No. 07/385,290, which is incorporated herein by reference. The release rates reported by Stockum, i.e., release from the coating over several hours, are not quick enough, however, to provide meaningful protection from viral pathogens. Moreover, we have found that gloves made by dipping cured gloves in an antimicrobial preparation suffer from significant activity loss on storage, and thus from poor reliability.

It is the objective of the present invention to provide surgical or examination gloves which rapidly release effective antiviral amounts of an antiinfective agent upon exposure to liquid, and which retain this ability over periods of prolonged storage.

SUMMARY OF THE INVENTION

In accordance with the present invention, an antiviral surgical or examination glove is obtained by blocking adsorption sites for the antiinfective agent which may exist in the lubricating agent, e.g., cross-linked corn starch, or in the material of the glove itself. The glove of the invention comprises an elastomeric hand-shaped body having interior and exterior surfaces and an inner coating disposed on the interior surface of the elastomeric body. The inner coating comprises (a) an antiinfective agent selected from the group consisting of chlorhexidine and pharmaceutically acceptable salts of chlorhexidine and (b) a lubricating agent which does not significantly adsorb the antiinfective agent. The inner coating is effective to deliver an antivirally effective amount of the antiinfective agent within ten minutes of exposure to a liquid. The preferred lubricating agent is corn starch modified with didecyldimethylammonium chloride.

DETAILED DESCRIPTION OF THE INVENTION

The present invention resides in an antiviral glove and in a method for preparing such a glove. The glove of the invention comprises an elastomeric hand-shaped body and an inner antiinfective coating.

The elastomeric body may be formed from any of a variety of materials known in the art for the manufacture of surgical or examination gloves including polyvinylchloride, polyurethane and silicone rubbers. Natural rubber latex is the preferred material, however, because of the flexibility and durability of this material.

The elastomeric body is formed in accordance with known procedures for the formation of gloves. Basically, these procedures involve preparing a fluid containing the elastomer, dipping a hand-shaped mandrel into the fluid to obtain a glove shaped coating, and coagulating, drying and curing the coating. The inner coating can be incorporated on the outside of the coated mandrel, either before or after the curing step, because the glove is inverted in the process of removing it from the mandrel.

The inner coating of the invention comprises chlorhexidine or a pharmaceutically acceptable salt of chlorhexidine as an antiinfective agent. Suitable salts of chlorhexidine include chlorhexidine gluconate, chlorhexidine acetate and chlorhexidine chloride.

The inner coating of the invention also includes a lubricating agent or donning aid to facilitate the putting on of the gloves. This lubricating agent is selected so that it does not significantly adsorb the antiinfective agent as this adsorption retards the release of the antiinfective agent, e.g., as in the Stockum patent. Suitable lubricating agents include zinc oxide, hydroxycellulose and corn starch, provided that the corn starch has been modified to block or saturate adsorption sites for the antiinfective agent. This can be accomplished using surfactants such as benzalkonium chloride or didecyldimethylammonium chloride. Gluconic acid has also been found to be useful for this purpose.

The inner coating may also incorporate one or more biomedically acceptable polymers. Suitable materials include polyurethanes and silicones which are dealt with at length in U.S. patent application Ser. No. 07/385,290 cited hereinabove. The use of these materials may be desirable to minimize the possibility of lubricating agent being released from the glove surface and to provide lubricity due to the nature of the polymeric component. Additional polymer materials may also reduce binding of the antiinfective agent to the latex, as these materials have less affinity for the antiinfective agent such that even if bound, the antiinfective agent is rapidly released from this surface.

The inner coating is formulated using nonadsorbent lubricating agents and sufficient antiinfective agent such that an effective antiviral amount of the antiinfective agent is released within ten minutes of being exposed to a fluid, e.g., blood, perspiration or other body fluid. Preferably the inner coating will provide substantially instantaneous release of the antiinfective agent so that any virus present is killed in the minimum possible time. We have found that concentrations of 300 $\mu$g/ml of chlorhexidine are sufficient to prevent infectivity by HBV or Rauscher's Leukemia Virus, an accepted model for HIV. Thus, given that the volume of fluid which could collect in a glove while it is being worn is less than 1.5 ml, one could assume that suitable antiviral levels would be achieved if there were about 4.5 mg of releasable antiinfective agent per glove. However, this assumes that all of the antiinfective agent would be released and that the fluid would not build up in one location for example, in one finger. To ensure that sufficient levels of antiinfective agent are reached in those circumstances as well, the gloves preferably include about 4.5 mg of releasable antiinfective agent per glove.

While this amount can be and advantageously is exceeded by a small amount to compensate for materials that are adsorbed, either by the lubricating agent or by the glove body itself, significant excesses of antiinfective agents should be avoided because these could lead to very high potentially toxic levels of antiinfective agent in the gloves. With these criteria in mind, the gloves of the invention preferably contain from 3.0 to 6.5 mg of active antiinfective agent per glove.

In addition to adsorption by the lubricating agent, the antiviral agent may also be adsorbed or otherwise made unavailable for release by the elastomeric glove body. This is particularly significant in the case of natural rubber gloves which have a high affinity for chlorhexidine. This type of adsorption appears to be a major factor in loss of activity on storage. Specifically, it appears that chlorhexidine originally present in the inner coating may be taken up over time by the glove body to be released slowly, if at all, on contact with fluids.

This problem of adsorption of the antiviral agent by the glove body leading to poor shelf stability can be solved in two ways. The first involves the manufacturing procedure of the glove, the second an additional material in the glove.

In the first approach to producing gloves with high shelf stability, the gloves are cast onto the mandrels and dried to form a film in the normal manner. Then, however, prior to curing the elastomeric body, the inner coating is supplied. In this case, the inner coating material contains an excess (about 10 fold) of the antiviral agent which is taken up by the elastomeric glove body to saturate its ability to adsorb the antiviral agent. This saturation process is accelerated by the heating occurring during the curing step. The antiviral agent in the inner coating thus cannot be adsorbed by the glove and remains available at a consistent level throughout the shelf life of the glove, generally a period of 6 months or longer.

While this approach to saturating the glove body is effective it has two potential drawbacks. First, a high level of antiinfective agent is actually present in the glove which may be released if the glove is worn for long periods of time. Secondly, using the antiinfective agent itself as the saturating agent is not very cost effective. For these reasons, it may be desirable to saturate adsorption sites in the glove body with a distinct material for this purpose. Suitable materials include metal ions or heavy metals such as zinc, silver, etc.; organic acids such as gluconic acid and surfactants preferably cationic surfactants such as Quarternary Ammonium Compounds.

Adsorption by the glove body can also be prevented by covering the exterior latex surface with a thin layer lubricating agent surfactant - treated silicone or polyurethane, and then coating with the inner coating layer containing the antiinfective agent and a nonadsorbent lubricating agent. Preferred materials for this thin layer are 2-5% silicone emulsion treated with didecyldimethylammonium chloride (sold under the trade name Bardac) or a 10% polyurethane. Adsorption by the glove can also be prevented by the use of weak acid and Bardac before high temperature cure. A suitable treatment involves application of 0.3% gluconic acid and 0.2% Bardac before the antiinfective agent.

In the case where a separate saturating material is used, this agent is advantageously added either to the original fluid for molding into the glove or between the drying and curing steps. The coating containing the antiviral itself is then applied either before or after curing of the glove body.

If polymeric materials such as silicones are to be included in the inner coating, the glove body should be saturated t block adsorption and the inner coating should be applied after curing of the glove body. In this way, reaction of the antiviral agent with the silicone polymer which might occur at the curing temperatures, thus bonding the antiviral in the inner coating and eliminating the quick release performance features of the glove is eliminated.

The invention will now be further described by way of the following specific examples. These examples are intended to demonstrate the efficacy of the invention and are not intended to limit the scope of protection.

EXAMPLE 1

Gloves in accordance with the invention were prepared from a dipping solution containing 33% natural rubber latex. To prepare this dipping solution 2000 ml of 60% TSC concentrate, latex was mixed with 1600 ml deionized/distilled water containing 1.6 ml of Bevaloid and stirred gently on a magnetic stirrer. In order to reduce foaming, the addition of a few more drops of Bevaloid was necessary. The Ph was adjusted to 10.0 using ammonium hydroxide and stirring continued for 10 minutes. The latex was then covered and allowed to stand for 20 minutes before use. Before dipping, the latex was stirred gently.

Hand-shaped glove forms were prepared for use by rinsing them with 1% Hcl and then with 0.6% ammonium hydroxide and drying at 100° C. for 20 minutes. The dried glove forms were then dipped in a coagulant bath (280 g of a mixture of calcium nitrate and calcium carbonate, and 1 ml Surfynol TG surfactant per 4000 ml of coagulant) at a temperature of 50° C. for 24 seconds. The coagulant coated glove forms were then dried for 75 seconds at 100° C. to prepare them for dipping in the latex dipping solution. The dip in the latex dipping solution had a duration of 15 seconds after which the partially formed gloves were dried at 100° C. for 5 minutes.

The dried partially formed gloves were next mechanically rolled to make a bead on the cuff and then immersed in a water bath at 80° C. for 3 minutes to leach out unwanted chemicals.

After the leaching step, the inner coating was formed by dipping the leached glove into a powder slurry containing 15% cornstarch, 0.2% Bardac 2250 and 2% chlorhexidine gluconate (CHG). To form this slurry 450 g of cornstarch was suspended in water and diluted to 2700 ml deionized water. 6 ml of Bardac 2250 was added to it and mixed well. This solution was mixed by placing on a magnetic stirrer and 300 ml of 20% CHG was added slowly and the mixing continued for 20 minutes. This slurry was then ready for use.

Finally, the CHG treated glove was dried in an oven at 100° C. for 1 hour to complete the gloves which were then removed from the forms.

EXAMPLE 2

The procedure of Example 1 is followed up to the stage of leaching the latex on the glove mold.

After the leaching step, the mold is dipped either into a solution containing 2% hydroxyethylcellulose (HEC)+1% silicone emulsion+0.2% Bardac or 10% polyurethane+0.2% Bardac.

The glove is cured in 100° C. oven for 1 hour. As soon as the glove comes out of the oven and while it is hot, it is dipped into a slurry containing 15% cornstarch+0.2% Bardac+2% CHG. This slurry is dried and the gloves removed from the molds.

EXAMPLE 3

The method of Example 1 was repeated except that the antiinfective slurry contained 5% zinc oxide+1% silicone emulsion+0.2% Bardac+either 1 or 2% chlorhexidine gluconate (CHG). Antiviral gloves were obtained providing instant release of the CHG.

EXAMPLE 4

The method of Example 1 was repeated except that the antiinfective slurry was 2% HEC+1% silicone emulsion+0.2% Bardac+1 or 2% chlorhexidine gluconate. Instant release antiviral gloves were obtained. The slurry may also have 1% zinc oxide.

EXAMPLE 5

The effect of aging on gloves prepared using our instant release method in which gloves are prepared without care to avoid adsorption.

PREPARATION OF COMPARATIVE GLOVES

1. The procedure of Example 1 is followed up to the stage of leaching the latex. After leaching, the glove is cured at 100° C. for one hour and then dipped into 8% cornstarch+2% CHG+0.5% silicone emulsion (LE46). The gloves are removed from the molds. (Table 1A).

TABLE 1A

| Drug Release and Retention of Comparative Glove | | |
|---|---|---|
| Age of Gloves (Days) | Amount of CHG/Finger (μg) | |
| | Bound to Latex | Released in Saline (10 Minutes Exposure) |
| 1 | 733 | 442 (100) |

TABLE 1A-continued

| Drug Release and Retention of Comparative Glove | | |
|---|---|---|
| Age of Gloves (Days) | Amount of CHG/Finger (μg) | |
| | Bound to Latex | Released in Saline (10 Minutes Exposure) |
| 3 | Not done | 401 (90) |
| 6 | Not done | 352 (80) |
| 16 | Not done | 343 (78) |
| 28 | Not done | 328 (74) |
| 64 | Not done | 230 (52) |
| 180 | 900 | 110 (24) |

Note: Figures in parentheses are a percentage of the first day's release.

2. The gloves are prepared according to the procedure described above, except that the antiinfective dip contain 12% cornstarch, 4% CHG and 1.42% silicone emulsion (LE46). (Table 2A).

TABLE 2A

| Rate of Release of CHG from Aged* Gloves Made by Comparative Method 2 | |
|---|---|
| Time (Minutes) | CHG Released/Finger (μg) |
| 10 | 193 |
| 30 | 276 |
| 60 | 340 |
| 120 | 392 |
| 240 | 361 |

3.0 ml of saline is place in each finger to extract the drug.
*The gloves were 6 months old at the time the above tests were done.

3. The gloves were prepared according to the procedure described in Stockum method (Example 1). Results in Table 2B.

TABLE 2B

| Effect of Aging of CHG-Glove* on the Release of CHG from the Glove Surface | |
|---|---|
| Time | CHG Released in 1 Minute (μg/finger) |
| 1 day post manufacture | 238 |
| 12 days post manufacture | 39 |

*Prepared according to Example 1, Stockum patent.

The results of these studies are shown in Table 1 and 2. In Table 1A, the effect of aging on comparative glove 1 is shown—with only 24% of the CHG originally available being released after 180 days. In contrast, during release by gloves in accordance with the invention is essentially constant over 6 months. (Table 1B)

TABLE 1B

| Drug Release and Retention of Gloves According to Example 1* | |
|---|---|
| Time | CHG in one finger (μg) |
| 1 week | 350 |
| 3 months | 360 |
| 6 months | 350 |

*Left at room temperature in open package.

Table 2B shows that in a glove according to Stockum Example 1, as little as 12 days is sufficient to cause a substantial (about 5-fold) decrease in drug release.

EXAMPLE 6

6 ml of TSB containing $10^4$ colony forming units (CFU) of *Staph. aureus* ATCC #10390 were exposed to the antiinfective agents as shown in Table 3 for 10 minutes. Aliquots were removed and diluted 1000 fold and 0.2 ml of the dilution was subcultured on 5% sheep's blood agar plates for colony counts. The results in Table 3 show the synergistic effect of Bardac and CHX against Staph. aureus.

TABLE 3

Synergistic Effect of CHG and Bardac against S. aureus after 10 Minute Exposure

| Drugs | Concentration of Drug (μg/6 ml Culture) | | | |
|---|---|---|---|---|
| CHG | 800 | 400 | 200 | |
| CFU/ml | 2 × 10⁴ | 2 × 10⁵ | 3 × 10⁵ | |
| Bardac | 40 | 20 | 10 | 5 |
| CFU/ml | 0 | 3 × 10⁴ | 1 × 10⁴ | 3 × 10⁶ |
| CHG | 400 | 400 | 400 | 200 |
| + Bardac | 40 | 20 | 10 | 20 |
| CFU/ml | 0 | 0 | 0 | 0 |
| None (Control) | 0 | — | — | — |
| CFU/ml | 5 × 10⁶ | — | — | — |

EXAMPLE 7

A slurry containing 2.5% CHG+8% cornstarch and varying concentrations of Bardac was prepared and used in making gloves in accordance with Example 1. Liquids were then added and the level of CHX in the supernatant was determined. The results indicate the CHX released from the cornstarch is proportional to the concentration of Bardac in the slurry (Table 4A). Table 4B shows the amount of CHG adsorbed on cross-linked cornstarch and surface modified cross-linked cornstarch (8% cornstarch slurry containing 0.5% Bardac was stirred for 1 hour). The results indicate that modified cornstarch adsorbs a significantly lower amount of drug and is unaffected by the contact period. Adsorption of drug on regular cornstarch is affected by the contact time.

TABLE 4A

Effect of Bardac on the Release of CHG

| Concentration of Bardac in Slurry (%) | % of CHG in Supernatant | |
|---|---|---|
| | 10 Minutes | 2 Hours |
| 0.0 | 1.6 | 1.6 |
| 0.2 | 1.8 | 1.7 |
| 0.4 | 2.0 | 2.0 |
| 0.6 | 2.2 | 2.1 |
| 0.8 | 2.3 | 2.2 |
| 1.0 | 2.5 | 2.5 |

TABLE 4B

Amount of Chlorhexidine in the Supernatant of CHG Slurry Containing Untreated Cornstarch and Surface Modified Cornstarch

| Slurry | % of CHG in Supernatant | |
|---|---|---|
| | 5 Hours* | 30 Hours* |
| 8% cornstarch + 2% CHG | 0.5 | 0.12 |
| 8% modified cornstarch** + 2% CHG | 1.0 | 1.0 |

*The drug content in supernatant was determined 5 and 30 hours after the addition of CHG to the slurry.
**Bardac is added to an 8% cornstarch slurry for a final concentration of 0.5% and then stirred for 1 hour followed by the addition of CHG.

It appears that Bardac interferes with the adsorption of chlorhexidine on cornstarch and also permits the rapid release of chlorhexidine. Thus, the use of Bardac in the coating slurry modifies the cornstarch surface and permits the instant release of chlorhexidine. As can be seen from Table 4A, all the drug adsorbed on the cornstarch is released immediately after the addition of Bardac. In addition, Bardac also acts synergistically with chlorhexidine in the rapid inactivation of fluid-borne viral and microbial pathogens. (Ex. 6)

EXAMPLE 8

Table 5 shows the amount of CHG released in 10 minutes from glove fingers coated with slurries of different compositions.

TABLE 5

Effect of the Coating Slurry Composition of Release of CHG

| Composition of Slurry | CHG/Finger (μg) |
|---|---|
| 12% cornstarch + 1% CHG | 65 |
| 12% cornstarch + 1% CHG + 0.2% Bardac | 88 |
| 12% cornstarch + 1% CHG + 0.4% Bardac | 165 |
| 12% cornstarch + 1% CHG + 0.3% Gluconic acid | 227 |

The above values are derived from a 10 minute release of drug from the fingers using 3 ml of saline.
Cornstarch treated with gluconic acid also includes instant release.

EXAMPLE 9

Antiinfective release levels were measured for a glove prepared in accordance with Example 1 as shown in Table 6A. For comparison, the release rates given in the Stockum Patent are also listed. As shown in Table 6B, the amount of chlorhexidine released from this glove is substantially constant over periods of time from 1 to 240 minutes.

TABLE 6A

CHG Release from A Glove Made According Example 1

| Time (Minutes) | CHG release (mg) |
|---|---|
| 1 | 4.5 |
| 10 | 4.5 |
| 30 | 4.6 |
| 60 | 4.9 |
| 120 | 4.8 |
| 240 | 4.8 |

TABLE 6B

CHG Release from Gloves Filled and Incubated with 50 ml of Saline Made by Two Different Methods

| Time (Minutes) | CHG-Bardac Method CHG/50 ml (mg) | Stockum Method* CHG/50 ml (mg) |
|---|---|---|
| 10 | 3.2 | unavailable |
| 30 | 3.4 | 0.150 |
| 60 | 3.6 | 0.155 |
| 120 | 3.6 | 0.230 |
| 240 | 3.6 | 0.342 |

*Results are taken from Stockum's patent and converted to common units.

EXAMPLE 10

An infectivity study using a Rauscher Leukemia Virus ("RLV") assay was conducted to determine the efficacy of stressed CHG-coated latex gloves challenged by a viral probe. It is known that when RLV is injected intravenously into mice, the live virus produces clear disease indicators (here, splenomegaly or weight increase) within 20 days from injection. The experiment sought to evaluate whether the CHG coating on the inner glove surface can perform a supplementary protective function in cases in which the latex glove barrier appears intact (without holes or visible breaks) and is impermeable to fluids, yet is semi-permeable to infectious viral particles. The protocol was designed to simulate the stressing of the latex glove barrier found in use situations.

Initial studies were performed to demonstrate potency of the virus, and that no apparent bias existed in the assignment of animals to any test group or controls. Animals used were six week old female Balb/c (ICR) mice. Pre-worn gloves were checked to make sure they had no pinholes or other breaks using a visual and a water test. Tests were conducted for the inventors in a double blind manner at an independent laboratory under the direction of Dr. Irving Millman.

10 ml of an RLV-infected mouse spleen homogenate was placed in a large glass test tube (the virus pool) with glove fingers stretched over the mouth. These glove fingers had been worn and subjected to physical manipulation before being stretched over a 50 ml beaker for 5 minutes. Six to seven glove fingers from Control (ordinary, uncoated glove fingers) and CHG-coated groups were processed similarly. 200 µl of buffer was placed in the tip of the glove finger. A glass pestle was used as a stretching rod to distend the glove into the virus pool for 20 stretches. Each stretch-release cycle extended approximately 3.5 times the length of the finger. After stretching, the glove finger was distended and held into the virus pool for 200 minutes, and then a 50 µl sample was taken from the exterior virus pool. All of the fluid was removed from the interior of the glove finger, and the empty glove finger was rinsed with 2 ml buffer and pooled with the interior fluid. The entire procedure was done on ice. Samples from the virus pool and the finger interiors were diluted to 4.8 ml and all the samples pelleted for 1 hour at 108,000 xg. The supernatant was aspirated, and the pelleted virus in the centrifuge tubes was frozen at $-70°$ C. overnight. The pellets were resuspended using 125 µl of Dulbecco's PBS. 25 µl was removed for a reverse transcriptase assay. The remaining 100 µl was removed for a reverse transcriptase assay. The remaining 100 µl was diluted with PBS to a final value of 250 µl and placed in a 1 ml syringe. The contents from each syringe were used to inject one six week old female Balb/c (ICR) mouse (tail vein injection). A group of 5 mice was injected with PBS to serve as negative (no virus) controls and 10 mice with diluted RLV stock to serve as positive controls.

After 20 days, all the animals were sacrificed, their spleens removed and weighed.

To summarize, the experimental groups consisted of mice tested with water from inside an uncoated glove, water from inside a coated glove, and the virus suspension outside either of the gloves. The experimental design and the mean spleen weight results are summarized in Table 7.

TABLE 7

| Glove inside/outside | CHG coating | Mean spleen weight in grams |
|---|---|---|
| outside | none | 0.2160 |
| outside | yes | 0.1900 |
| inside | none | 0.1245 |
| inside | yes | 0.0888 |

Analyses of variance in the experimental groups showed the latex glove barrier itself had the greatest effect on spleen weights; the CHG coating had less of an effect, but the data suggest it is important.

The comparison of greatest interest was between the inside of the gloves with or without the CHG coating. The analysis revealed highly significant results demonstrating the enhanced protective effect of CHG-coated gloves. The data showed that one mouse in the group receiving the liquid from inside the uncoated gloves had a spleen weight of 0.1707 g, strongly suggesting viral infection had definitely occurred. If correct, this indicated that at least one of six mice from the uncoated gloves had picked up the virus, versus none of seven from the CHG-coated gloves.

Because of the possible importance of this observation, statistical analysis was carried out with a data set consisting only of mice treated with the liquid from inside the gloves, either coated or uncoated. This analysis demonstrated a significant difference in mean spleen weights between coated and uncoated gloves at the $p<0.05$ level. The comparison between these valves and the positive and negative controls is shown in Table 8.

TABLE 8

| Group | Mean spleen weight 20 days post-injection (grams) |
|---|---|
| Positive Control (Virus in buffer) | 0.2160 |
| Negative Control (No virus in buffer) | 0.095 |
| Control glove interior | 0.1245 |
| CHG-glove interior | 0.0888 |

From these data, it appears that some live viruses or infectious viral particles can pass through the stressed latex as indicated by the increased spleen size in Control glove fingers (0.125 g). When viruses pass through CHG-coated gloves, they are inactivated and are not infective as indicated by the spleen size (0.09 g), which is similar to that of the Control group suing no virus.

Furthermore, every mouse injected with liquid from the inside of a CHG-coated glove had a spleen weight of 0.1 g or less (comparable to no virus Control); in contrast, every mouse injected with liquid from the interior of an uncoated glove had a spleen weight of 0.1 g or greater, with one mouse having an extremely high weight of 0.17 g. See Table 9 for the test results. (These results, demonstrating passage of such viral particles through "semi-permeable" latex barriers compromised by stretching but free of macroscopic defects, are consistent with other research findings, e.g., Goldstein et al., "Small Particle Permeability of Stressed Latex Rubber Barriers.")

TABLE 9

| Individual Spleen Weights (grams) | | |
|---|---|---|
| Negative control (no virus in buffer) | Uncoated glove interior | CHG-coated glove (interior) |
| .0834 | .1297 | .0959 |
| .0861 | .1707 | .0786 |
| .0948 | .1079 | .0917 |
| .1156 | .1227 | .0802 |
| .0908 | .1196 | .0899 |
| .1000 | .1026 | .1018 |
| | | .0833 |

The results demonstrate the supplementary protective effect of the CHG coating when the latex barrier becomes permeable to infectious viral particles due to stretching, but appears "physically intact." In the study, the CHG coating was effective against the occasional passage of virus through compromised, semi-permeable gloves. The mean of coated gloves was clearly the closest to the negative control of no virus at al, whereas in the absence of the coating, there was a consistent trend toward higher measures of viral presence, and at least one strong case of infection approaching the mean for glove exteriors.

We claim:

1. An antiviral glove consisting essentially of an elastomeric hand-shaped body having interior and exterior surfaces and an inner coating disposed on the interior surface of the elastomeric body, wherein the inner coating comprises (a) an antiinfective agent selected from the group consisting of chlorhexidine and pharmaceutically acceptable salts of chlorhexidine and (b) a lubricating agent which does not significantly adsorb the antiinfective agent, said inner coating being effective to deliver an antivirally effective amount of the antiinfective agent within ten minutes of exposure to a liquid.

2. An antiviral glove according to claim 1, wherein the delivery of antiinfective agent from the inner coating is substantially complete within ten minutes of exposure to liquid.

3. An antiviral glove according to claim 1, wherein the lubricating agent is corn starch modified with didecyldimethylammonium chloride.

4. An antiviral glove according to claim 3, wherein the elastomeric body is formed from a natural rubber latex.

5. An antiviral glove according to claim 4, wherein the natural rubber latex is modified to saturate binding sites for the antiinfective agent in the latex.

6. An antiviral glove according to claim 5, wherein the latex is saturated with a material selected from the group selected from metal ions, organic acids and cationic surfactants.

7. An antiviral glove according to claim 1, wherein the inner coating further comprises a biomedically acceptable polymer.

8. An antiviral glove according to claim 7, wherein the polymer is selected from the group consisting of silicones and polyurethanes.

9. An antiviral glove according to claim 1, wherein the elastomeric body is formed from a natural rubber latex.

10. An antiviral glove according to claim 9, wherein the natural rubber latex is modified to saturate binding sites for the antiinfective agent in the latex.

11. An antiviral glove according to claim 10, wherein the latex is saturated with a material selected from the group consisting of metal ions, organic acids and cationic surfactants.

12. An antiviral glove according to claim 1, wherein the lubricating agent is zinc oxide.

13. An antiviral glove according to claim 1, wherein the glove contains from 3.0 to 6.5 mg of releasable antiinfective agent.

* * * * *